United States Patent [19]

Wu

[11] Patent Number: 5,157,153

[45] Date of Patent: Oct. 20, 1992

[54] PREPARATION OF PHOSPHINOACETIC ACIDS

[75] Inventor: An-hsiang Wu, Bartlesville, Okla.

[73] Assignee: Phillips Petroleum Company, Bartlesville, Okla.

[21] Appl. No.: 790,790

[22] Filed: Nov. 12, 1991

[51] Int. Cl.$^5$ .................... C07C 51/16; C07C 53/00; C07C 69/00; C07C 205/00

[52] U.S. Cl. .................... 562/512; 562/537; 562/405; 562/8; 560/129; 560/125; 560/8

[58] Field of Search .................. 562/537, 512, 405, 8; 560/129, 125, 8

[56] References Cited

PUBLICATIONS

K. Issleib and G. Thomas, "Darstellung von Carboxyphosphinen R$_2$P[CH$_2$]$_n$—CO$_2$H", Chem. Berichte 93, 1960, pp. 803–808.
M. A. Kakli et al., "The Preparation and Characterization of Solve Phosphinoacetic Acids, Salts, and Esters", Syn. React. Inorg. Metal-Org. Chem. 5, 1975, 357–371.
T. Jarolim et al., "Coordinating Behaviour of Diphenylphosphine-acetic Acid", J. Inorg. Nucl. Chem., 38, 1976, pp. 125–129.
M. Peuckert and W. Keim, "A New Nickel Complex for the Oligomerization of Ethylene", Organometallics 1983, 2, pp. 594–597.

Primary Examiner—Jose G. Dees
Assistant Examiner—Keith MacMillan
Attorney, Agent, or Firm—K. K. Brandes

[57] ABSTRACT

P,P-dihydrocarbylphosphinoacetic acids are prepared by reacting an alkyl ethynyl ether (preferably ethyl ethynyl ether) and/or a haloacetaldehyde acetal (preferably bromoacetaldehyde diethyl acetal) with a basic alkali metal compound (preferably lithium diisopropylamide), followed by coupling with a least one halodihydrocarbylphosphine (preferably chlorodiphenylphosphine or chlorodiethylphosphine or chlorodi(t-butyl)phosphine or chlorodicyclohexylphosphine) and subsequent hydrolysis.

23 Claims, No Drawings

PREPARATION OF PHOSPHINOACETIC ACIDS

BACKGROUND OF THE INVENTION

This invention relates to the preparation of P,P-dihydrocarbylphosphinoacetic acids, which are useful as intermediates in the preparation of ethylene oligomerization catalysts. In one particular aspect, this invention relates to the preparation of P,P-diarylphosphinoacetic acid. In another particular aspect, this invention relates to the preparation of P,P-dialkylphosphinoacetic acids. In a further particular aspect, this invention relates to the preparation of P,P-dicycloalkylphosphinoacetic acids.

P,P-disubstituted phosphinoacetic acids of the type $R_2P-CH_2-CO_2H$ are known, and their preparation has been described in Chemische Berichte 93, 1960, pages 803-808. The preparation method described in this article comprises the steps of reacting a dihydrocarbyl-substituted alkali metal phosphide, e.g., $KP(C_6H_5)_2$, with a haloacetate, e.g., ethyl chloroacetate, and hydrolyzing the formed dihydrocarbylphosphinoacetatic acid ester with an alcoholic sodium hydroxide solution and thereafter with sulfuric acid. This prior art synthesis requires the use of very reactive alkali metal phosphides. The present invention is directed to a less dangerous, more practical synthesis of P,P-dihydrocarbylphosphinoacetic acids which does not involve the use of alkali metal phosphides.

SUMMARY OF THE INVENTION

It is an object of this invention to prepare P,P-dihydrocarbylphosphinoacetic acids. It is another object of this invention to prepare a P,P-dihydrocarbylphosphinoacetic acid from an alkyl ethynyl ether. It is a further object of this invention to prepare a P,P-dihydrocarbylphosphinoacetic acid from a haloacetaldehyde acetal. It is one particular object of this invention to prepare P,P-diarylphosphinoacetic acids. It is another particular object of this invention to prepare P,P-dialkylphosphinoacetic acids. It is a further particular object of this invention to prepare P,P-dicycloalkylphosphinoacetic acid. Other objects and advantages will be apparent from the detailed description of the invention and the appended claims.

In accordance with this invention, a process for preparing at least one P,P-dihydrocarbylphosphinoacetic acid comprises the steps of:

(1) reacting at least one reagent selected from the group consisting of alkyl ethynyl ethers and monohaloacetaldehyde acetals with at least one basic compound of the general formula MZ, wherein M is an alkali metal and Z can be $-H$ or $-OR'$ or $-NH_2$ or $-NHR'$ or $-N(R')_2$, with R' being an alkyl or cycloalkyl group having 1-8 carbon atoms, at a temperature at least about $-30°$ C. for a time period of at least about 1 second;

(2) contacting the reaction mixture obtained in step (1) with at least one halodihydrocarbylphosphine having the general formula of $R_2PX$, wherein X is Cl or Br or I, and each R is independently selected from the group consisting of alkyl groups containing 1-10 carbon atoms, cycloalkyl groups containing 3-10 carbon atoms and aryl groups containing 6-12 carbon atoms, and maintaining the thus obtained mixture at a temperature of at least about $-30°$ C. for a time period of at least about 1 second;

(3) adding to the reaction mixture obtained in step (2) at least one mineral acid and maintaining the thus-obtained mixture under such conditions as to form at least one P,P-dihydrocarbylphosphinoacetic acid ester;

(4) hydrolyzing said at least one P,P-dihydrocarbyphosphinoacetic acid ester under such conditions as to obtain a reaction mixture comprising said at least one P,P-dihydrocarbylphosphinoacetic acid; and (5) recovering said at least one P,P-dihydrocarbylphosphinoacetic acid from the reaction mixture obtained in step (4).

In one preferred embodiment, each hydrocarbyl group R in $R_2PX$ (defined above) can be an alkyl group containing 1-6 carbon atoms or a cycloalkyl (including alkyl-substituted cycloalkyl) group containing 5-7 carbon atoms or an aryl (including alkyl-substituted or cycloalkyl-substituted or alkylcycloalkyl-substituted aryl) group containing 6-8 carbon atoms, and X is Cl or Br, more preferably Cl.

In another preferred embodiment, the basic compound used in step (1) is at least one alkali metal dialkylamide, more preferably $LiN(R')_2$, wherein each R' is an alkyl group as defined above (preferably containing 2-4 carbon atoms). In a further preferred embodiment, the agent used in step (1) is at least one alkyl ethynyl ether, $HC≡C-O-R''$, wherein the alkyl group R'' contains 1-8 carbon atoms. In still another preferred embodiment, the agent used in step (1) is at least one monohaloacetaldehyde acetal, $X-CH_2-CH(OR'')_2$, wherein each R'' is independently selected from alkyl groups containing 1-8 carbon atoms and X is Cl or Br, more preferably Br.

In a still further preferred embodiment, hydrolysis step (4) is carried out in two sub-steps: (4a) treating the at least one P,P-dihydrocarbylphosphinoacetic acid ester formed in step (3) with at least one dissolved alkali metal hydroxide under such conditions as to form at least one alkali metal salt of said at least one diphenylphosphinoacetic acid, and (4b) contacting the reaction mixture obtained in step (4a) with at least one mineral acid defined above under such conditions as to form said at least one P,P-dihydrocarbylphosphinoacetic acid.

DETAILED DESCRIPTION OF THE INVENTION

The reagents which are used in the process of this invention are known. They are either commercially available or can be prepared by known methods.

The basic compounds of the general formula MZ, as defined above, which are used in step (1), are known and can be prepared by reaction of an alkali metal with either $H_2$ or an alcohol or ammonia or an amine. The preferred basic compound used in step (1) is lithium diisopropyl amide, which is commercially available from Pfaltz & Bauer, Stamford, Conn. or the MCB Manufacturing Division of E. Merck, Cincinnati, Ohio.

Alkyl ethynyl ethers, which can be used in step (1), are known and can be prepared by the reaction of haloacetaldehyde dialkyl acetals and a strong base. Preferably, the alkyl groups contain 1-3 carbon atoms. The most preferred alkyl ethynyl ether is ethyl ethynyl ether, which can be prepared by the reaction of bromoacetaldehyde diethyl acetal and a strong base, and is commercially available from Chemsample, Columbus, Ohio.

The other type of reagent, which can be used in step (1), namely haloacetaldehyde acetal(s), is also known.

Preferably, the acetals are dialkyl acetals wherein each alkyl group can contain 1-8 carbon atoms, more preferably 1-3 carbon atoms. These haloacetaldehyde dialkyl acetals can be prepared by the reaction of one mole of a haloacetaldehyde (preferably cholor- or bromoacetaldehyde) with one or, preferably, two mols of an alcohol containing 1-8, more preferably 1-3, carbon atoms per molecule.

The most preferred haloacetaldehyde acetal, bromoaldehyde diethyl acetal, is commercially available from Pfaltz & Bauer, Stamford, Conn., and from the MCB Manufacturing Division of E. Merck, Cincinnati, Ohio.

Halodihydrocarbylphosphines which are used in step (2) are known and can be prepared by the reaction of a phosphorous trihalide (in particular $PCl_3$) with 2 equivalents of a hydrocarbylmagnesium halide (in particular an alkylmagnesium chloride or alkylmagnesium bromide). Preferred chlorodialkylphosphines, such as chlorodiethylphosphine, chlorodi(t-butyl)phosphine, chlorodicyclohexylphosphine and chlorodiphenylphosphine, are commercially available, e.g., from Strem Chemicals, Inc., Newburyport, Mass. Other examples of suitable halohydrocarbylphosphines include fluorodimethylphosphine, chlorodimethylphosphine, bromodimethylphosphine, iododimethylphosphine, fluorodiethylphosphine, bromodiethylphosphine, iododiethylphosphine, chlorodipropylphosphine, chlorodi(n-butyl)phosphine, chlorodiphenylphosphine, chlorodihexylphosphine, chloromethylethylphosphine (and other mixed haloalkylphosphines), fluorodicyclopentylphosphine, chlorodicyclopentylphosphine, bromodicyclopentylphosphine, iodocyclopentylphosphine, fluorodicyclohexylphosphine, bromodicyclohexylphosphine, iododicyclohexylphosphine, fluorodiphylphosphine, bromodiphenylphosphine, iododiphenylphosphine, fluoroditolyphosphine, chloroditolyphosphine, bromoditolylphosphine, iododitolyphosphine and the like, and mixtures of any of the above compounds.

Step (1) of the process of this invention is carried out under such conditions as to form an intermediate compound of the general formula MC≡C—O—R'', wherein M is an alkali metal and R'' is an alkyl group, as defined above. The reaction temperature in step (1) generally is in the range of about −30° to about 50° C., and preferably is in the range of about −10° C. to about 20° C. The reaction time generally ranges from about 1 minute to about 1 hour, and preferably is in the range of about 10 to about 40 minutes. Generally, the molar ratio of the at least one basic compound MZ to the at least one alkyl ethynyl ether (when used) is about 1:1 to about 1.5:1, whereas the molar ratio of the at least one basic compound MZ to the at least one haloacetaldehyde acetal (when used) is about 3:1 to about 4:1. Preferably, the reagents used in step (1) are dissolved in a suitable solvent (such as an ether).

Step (2) of the process of this invention is carried out in any suitable manner, generally at a temperature in the range of about −30° C. to about 50° C. (preferably about −10° C. to about 50° C.) for a time sufficient to substantially replace the alkali metal in the intermediate compound formed in step (1) with the —$PR_2$ group while alkali metal halide is formed as a by-product, which generally requires a reaction time of about 4 minutes to about 2 hours. Generally, the halodihydrocarbylphosphine (preferably dissolved in a suitable solvent, such as an ether) is added to the reaction mixture obtained in step (1) with agitation, preferably during a period of time of about 1 minute to about 30 minutes (preferably about 5-20 minutes), at a temperature of about −10° C. to about 10° C. Thereafter, the obtained mixture is generally maintained at that temperature for about 0.5-100 minutes. Then the temperature is generally raised to about 10°-50° C., and the reaction mixture is maintained at this higher temperature for about 0.5-100 minutes. Generally, the molar ratio of halodihydrocarbylphosphine to alkyl ethynyl ether or haloacetaldehyde acetal employed in step (1) is about 0.9:1 to about 1.2:1.

Step (3) of the process of this invention is carried out in any suitable manner under such conditions as to substantially hydrolyze the intermediate compound formed in step (2) to at least one P,P-dihydrocarbylphosphinoacetate (i.e., an ester of P,P-dihydrocarbylphosphinoacetic acid). Step (3) is carried out by treating (generally with agitation) the completed reaction mixture of step (2), preferably after the solvent has been substantially removed therefrom (as has been disclosed in the examples), with an aqueous solution of at least one mineral with an aqueous solution of at least one mineral acid, preferably HCl or $H_2SO_4$ or $HNO_3$, or mixtures thereof, preferably an acid solution having a normality of about 0.5-5. Generally, the pH of the reaction mixture in step (d) is about 0-4, the reaction temperature is in the range of about 60° to about 100° C., and the reaction time is about 0.1 to 5 hours.

Preferably, the formed at least one P,P-dihydrocarbylphosphinoacetic acid ester is recovered in an additional step (3a) from the completed reaction mixture obtained in step (3). This recovery step (3a) can be carried out in any suitable manner. In a preferred mode (described in the examples), the formed ester is extracted from the completed acidic reaction mixture obtained in step (3) by means of a suitable organic solvent, which exhibits little solubility in water (such as an ether), followed by drying and evaporation of the solvent.

Hydrolysis step (4) can be carried out under such effective reaction conditions as to substantially convert the P,P-dihydrocarbylphosphinoacetate(s) formed in step (3) to P,P-dihydrocarbylphosphinoacetic acid(s). It would be possible to carry out step (4) by extending hydrolysis step (3), after the addition of additional concentrated acid, for a long time, such as about 0.5-3 days. However, it is preferred to carry out hydrolysis step (4) in two substeps. In sub-step (4a), the at least one ester obtained in step (3a) is generally treated with a solution (preferably aqueous) of at least one alkali metal hydroxide, preferably KOH, containing about 5-30 weight percent of the alkali metal hydroxide, at a temperature of about 60° to about 100° C. for a period of time of about 5-60 minutes, so as to substantially convert the ester(s) to at least one alkali metal salt of at least one P,P-dihydrocarbylphosphinoacetic acid. In the subsequent sub-step (4b), the alkaline reaction mixture obtained in step (4a) is acidified with a mineral acid, such as a concentrated (preferably 10-50 weight-%) aqueous solution of HCl, generally with cooling to about 0°-10° C., under such conditions as to precipitate the at least one P,P-dihydrocarbylphosphinoacetic acid.

Recovery step (5) can be carried out in any suitable manner. Preferably, the formed P,P-dihydrocarbylphosphinoacetic acid is separated from the completed reaction mixture by filtration and drying. Alternatively, the formed acid can be extracted, preferably by means of an ether or any other effective solvent which is substantially immiscible in water, followed by evaporation of the solvent. The thus obtained crystalline P,P-dihydrocarbylphosphinoacetic acid can be further purified by dissolving it in an aqueous alkali metal hydroxide solution, followed by acidification with one of the above-mentioned mineral acids, and separating the purified P,P-dihydrocarbylphisphinoacetic acid from the acidic solution (e.g., by filtration).

The hydrocarbyl groups in the produced P,P-dihydrocarbylphosphinoacetic acid are the same as the R groups defined above for the halodihydrocarbylphosphine, i.e., alkyl groups with 1-10 carbon atoms or cycloalkyl groups containing 3-10 carbon atoms and aryl groups containing 6-10 carbon atoms. Preferred P,P-dihydrocarbylphosphinoacetic acids are demthylphosphinoacetic acid, diethylphosphinoacetic acid, methylethylphosphinoacetic acid, dipropylphosphinoacetic acid, di(n-butyl)phosphinoacetic acid, di(t-butyl)phosphinoacetic acid, dicyclohexylphosphinoacetic acid, diphenylphosphinoacetic acid, ditolylphosphinoacetic acid, and the like.

The following examples are presented to further illustrate the claimed invention and are not to be construed as unduly limiting the scope of this invention.

EXAMPLE I

This example illustrates the preparation of dihydrocarbylphosphinoacetic acids from an alkyl ethnyl ether in accordance with this invention. Essentially all lab-grade reagents used in the preparations described in this example had been supplied by Aldrich Chemical Company, a subsidiary of Sigma-Aldrich Corporation, Milwaukee, Wis.

During a period of 5 minutes, 7 ml of a 1.5 molar solution of lithium diisopropylamide in tetrahydrofuran, containing 10.5 millimols of $LiN(C_3H_6)_2$, were added to a well agitated mixture of 1.40 g of a 50 weight-% solution of ethyl ethynyl ether in n-hexane (containing 10 millimols of the ether) and 10 mL of dry tetrahydrofuran, at a temperature of about 0° C. under a nitrogen gas atmosphere. This reaction mixture was stirred for about 30 minutes at 0° C. Then a solution containing 220 g (10 millimols) of chlorodiphenylphosphine in dry tetrahydrofuran was added by means of a syringe during a period of time of 10 minutes. Thereafter, this reaction mixture was stirred at 0° C. for about 30 minutes, allowed to warm to room temperature (by removing an external ice bath), and stirred for 30 minutes at room temperature.

The solvent of the completed reaction mixture was evaporated under vacuum conditions, and a yellow oil was obtained as the residue, which was then heated under reflux conditions for 3 hours with 40 mL of aqueous 3N hydrochloric acid. This reaction mixture was cooled to room temperature and extracted three times with 50 mL aliquots of diethyl ether. The three ether extracts were combined, dried over anhydrous $MgSO_4$, filtered and subjected to vacuum evaporation. The residue (comprising primarily ethyl diphenylphosphinoacetate) was heated with 30 mL of a 10 weight-% aqueous KOH solution for 15 minutes at 70°-80° C. The alkaline solution was cooled and extracted three times with 50 mL aliquots of methylene chloride. The organic (methylene chloride) phases were discarded, while the aqueous raffinate was acidified by the slow addition of aqueous hydrochloric acid (38 weight-% HCl) at a temperature of about 0° C. The acidified solution was filtered, and the filter cake containing diphenylphosphinoacetic acid which was dried. The weight of dry, colorless, microcrystalline diphenylphosphinoacetic acid, which melted at 119° C., was 1.98 grams (8.1 millimols) thus corresponding to a yield of 81%, based on the weight of ethyl ethynyl ether.

Additional preparations in accordance with the above-described procedures were carried out with chlorodicyclohexylphosphine, chlorodi(tertiary-butyl)phosphine and chlorodiethylphosphine, respectively, in lieu of chlorodiphenylphosphine, thus producing dicyclohexylphosphinoacetic acid (melting point: 85° C.) at a yield of 83%, di(tertiary-butyl)phosphinoacetic acid (melting point: 71° C.) at a yield of 77%, and diethylphispinoacetic acid (melting point: 96° C.) at a yield of 84%, respectively.

EXAMPLE II

This example illustrates the preparation of dihydrocarbylphosphinoacetic acids from a bromoacetaldehyde dialkyl acetal in accordance with this invention. Essentially all lab-grade reagents used in the preparations described in this example had been supplied by Aldrich Chemical Company, a subsidiary of Sigma-Aldrich Corporation, Milwaukee, Wis.

During a period of 5 minutes, 21 mL of a 1.5 molar solution of lithium diisopropylamide in tetrahydrofuran, containing 31.5 millimols of $LiN(C_3H_7)_2$, were added to a well agitated solution of 1.97 g bromoacetaldehyde diethyl acetal (10.0 millimols) in tetrahydrofuran, at a temperature of 0° C. under a nitrogen gas atmosphere. This reaction mixture was stirred for about 60 minutes at 0° C. Then a solution containing 2.20 g (10 millimols) of chlorodiphenylphosphine in dry tetrahydrofuran was added by means of a syringe during a period of of 10 minutes. Thereafter, this reaction mixture was stirred at 0° C. for 60 minutes, allowed to warm to room temperature (by removing an external ice bath), and stirred for 60 minutes at room temperature.

The solvent of the reaction mixture was evaporated under vacuum conditions, and a yellow oil was obtained as the residue, which was then heated under reflux conditions for 3 hours with 40 mL of aqueous 3N hydrochloric acid. This reaction mixture was cooled to room temperature and extracted three times with 50 mL aliquots of diethyl ether. The three ether extracts were combined, dried over anhydrous $MgSO_4$, filtered and subjected to vacuum evaporation. The residue (comprising primarily ethyl diphenylphosphinoacetate) was heated with 30 mL of a 10 weight-% aqueous KOH solution for 15 minutes at 70°-80° C. The alkaline solution was cooled and extracted three times with 50 mL aliquots of methylene chloride. The aqueous raffinate was slowly acidified by the addition of an aqueous 38 weight-% HCl solution at 0° C. The precipitated diphenylphosphinoacetic acid was recovered by filtration, dried and weighed. The yield of the dry, colorless, microcrystalline diphenylphosphinoacetic acid (melting point: 119° C.) was 1.73 grams (7.1 millimols), thus corresponding to a yield of 71%, based on the weight of bromoacetaldehyde diethyl acetal.

Additional preparations in accordance with the above-described procedures were carried out with chlorodicyclohexylphosphine, chlorodi(tertiary-butyl)phosphine and chlorodiethylphosphine, respectively, in lieu of chlorodiphenylphosphine, thus producing dicyclohexylphosphinoacetic acid (melting point: 86° C.) at a yield of 67%, di(tertiary-butyl)phosphinoacetic acid (melting point: 71° C.) at a yield of 64% and diethylphosphinoacetic acid (melting point: 94° C.) at a yield of 70%, respectively.

Reasonable variations, modifications and adaptations, for various conditions can be made within the scope of the disclosure and the appended claims, without departing from the scope of the invention.

That which is claimed is:

1. A process for preparing at least one P,P-dihydrocarbylphosphinoacetic acid comprising the steps of:
   (1) reacting at least one reagent selected from the group consisting of alkyl ethynyl ethers and monohaloacetaldehyde acetals with at least one basic compound of the general formula MZ, wherein M is an alkali metal and Z can be —H or OR' or —$NH_2$ or —NHR' or —$N(R')_2$, with R' being an alkyl or cycloalkyl group having 1–8 carbon atoms, at a temperature of at least about −30° C. for a period of time of at least 1 second;
   (2) contacting the reaction mixture obtained in step (1) with at least one halodihydrocarbylphosphine having the general formula of $R_2PX$, wherein X is Cl or Br or I, and each R is independently selected from the group consisting of alkyl groups containing 1–10 carbon atoms, cycloalkyl groups containing 3–10 carbon atoms and aryl groups containing 6–12 carbon atoms, and maintaining the thus obtained mixture at a temperature of at least −30° C. for a time period of at least 1 second;
   (3) adding to the reaction mixture obtained in step (2) at least one mineral acid and maintaining the thus-obtained mixture under such conditions as to form at least one P,P-dihydrocarbylphosphinoacetic acid ester;
   (4) hydrolyzing said at least one P,P-dihydrocarbylphosphinoacetic acid ester under such conditions so as to obtain a reaction mixture comprising at least one P,P-dihydrocarbylphosphinoacetic acid; and
   (5) recovering said at least one P,P-dihydrocarbylphosphinoacetic acid from the reaction mixture obtained in step (4).

2. A process in accordance with claim 1, wherein said at least one basic compound used in step (1) is at least one alkali metal dialkylamide.

3. A process in accordance with claim 2, wherein said at least one alkali metal dialkylamide is at least one lithium dialkylamide.

4. A process in accordance with claim 1, wherein said at least one reagent used in step (1) is at least one alkyl ethynyl ether with the alkyl group containing 1–8 carbon atoms.

5. A process in accordance with claim 1, wherein said at least one reagent used in step (1) is ethyl ethynyl ether and said at least one basic compound used in step (1) is lithium diisopropylamide.

6. A process in accordance with claim 1, wherein said at least one reagent used in step (1) is at least one bromoacetaldehyde dialkyl acetal with each alkyl group containing 1–8 carbon atoms.

7. A process in accordance with claim 1, wherein said at least one reagent used in step (1) is bromoacetaldehyde diethyl acetal and said at least one basic compound used in step (1) is lithium diisopropylamide.

8. A process in accordance with claim 1, wherein step (1) is carried out at a temperature of about −30° C. to about 50° C. for a period of time of about 1 minute to about 1 hour.

9. A process in accordance with claim 1, wherein said at least one halodihydrocarbylphosphine used in step (2) is at least one chlorodihydrocarbylphosphine.

10. A process in accordance with claim 1, wherein said at least one halodihydrocarbylphosphine used in step (2) is chlorodiphenylphosphine, and said at least one P,P-dihydrocarbylphosphinoacetic acid formed in step (4) and recovered in step (5) is P,P-diphenylphosphinoacetic acid.

11. A process in accordance with claim 10, wherein said at least one reagent used in step (1) is selected from the group consisting of ethyl ethynyl ether and bromoacetaldehyde diethyl acetal and said at least one basic compound used in step (1) is lithium diisopropylamide.

12. A process in accordance with claim 1, wherein said at least one halodihydrocarbylphosphine used in step (2) is chlorodiethylphosphine, and said at least one P,P-dihydrocarbylphosphinoacetic acid formed in step (4) and recovered in step (5) is P,P-diethylphosphinoacetic acid.

13. A process in accordance with claim 12, wherein said at least one reagent used in step (1) is selected from the group consisting of ethyl ethynyl ether and bromoacetaldehyde diethyl acetal and said at least one basic compound used in step (1) is lithium diisopropylamide.

14. A process in accordance with claim 1, wherein said at least one halodihydrocarbylphosphine used in step (2) is chlorodi(tertiary-butyl)phosphine, and said at least one P,P-dihydrocarbylphosphinoacetic acid formed in step (4) and recovered in step (5) is P,P-di(tertiary-butyl)phosphinoacetic acid.

15. A process in accordance with claim 14, wherein said at least one reagent used in step (1) is selected from the group consisting of ethyl ethynyl ether and bromoacetaldehyde diethyl acetal and said at least one basic compound used in step (1) is lithium diisopropylamide.

16. A process in accordance with claim 1, wherein said at least one halodihydrocarbylphosphine used in step (2) is chlorodicyclohexylphosphine, and said at least one P,P-dihydrocarbylphosphinoacetic acid formed in step (4) and recovered in step (5) is P,P-dicyclohexylphosphinoacetic acid.

17. A process in accordance with claim 16, wherein said at least one reagent used in step (1) is selected from the group consisting of ethyl ethynyl ether and bromoacetaldehyde diethyl acetal and said at least one basic compound used in step (1) is lithium diisopropylamide.

18. A process in accordance with claim 1, wherein step (2) is carried out at a temperature of about −30° C. to about 50° C. for a period of time of about 2 minutes to about 4 hours.

19. A process in accordance with claim 1, wherein step (3) is carried out with an aqueous solution of at least one mineral acid selected from the group consisting of HCl, $HNO_3$ and $H_2SO_4$.

20. A process in accordance with claim 19, wherein said aqueous solution of said at least one mineral acid used in step (3) has a normality of about 0.5–5, and step (3) is carried out at a temperature of about 60°–100° C. for a period of time of about 0.1–5 hours.

21. A process in accordance with claim 1 comprising the additional step (3a) of recovering said at least one P,P-dihydrocarbylphosphinoacetic acid ester from the completed reaction mixture obtained in step (3).

22. A process in accordance with claim 1, wherein step (4) is carried out in two sub-steps:
   (4a) treating the at least one P,P-dihydrocarbylphosphinoacetic acid ester with at least one dissolved alkali metal hydroxide under such conditions as to form at least one alkali metal salt of said at least one diphenylphosphinoacetic acid, and
   (4b) contacting the reaction mixture obtained in step (4a) with at least one mineral acid under such conditions so as to form said at least one P,P-dihydrocarbylphosphinoacetic acid.

23. A process in accordance with claim 22, wherein sub-step (4a) is carried out with an aqueous solution of KOH at a temperature of about 60°–100° C., and sub-step (4b) is carried out with an aqueous solution of hydrochloric acid.

* * * * *